(12) United States Patent
Harrison et al.

(10) Patent No.: US 10,328,029 B2
(45) Date of Patent: Jun. 25, 2019

(54) PHARMACEUTICAL COMPOSITION

(71) Applicant: Cycle Pharmaceuticals, Cambridge, Cambridgeshire (GB)

(72) Inventors: James Harrison, Little Shelford (GB); Stephen Fuller, Cambridge (GB); Tobias Josef Brown, Cambridge (GB)

(73) Assignee: CYCLE PHARMACEUTICALS LTD, Cambridge, Cambridgeshire (GB)

( * ) Notice: Subject to any disclaimer, the term of this patent is extended or adjusted under 35 U.S.C. 154(b) by 0 days.

(21) Appl. No.: 15/109,220

(22) PCT Filed: Jan. 5, 2015

(86) PCT No.: PCT/GB2015/050006
§ 371 (c)(1),
(2) Date: Jun. 30, 2016

(87) PCT Pub. No.: WO2015/101794
PCT Pub. Date: Jul. 9, 2015

(65) Prior Publication Data
US 2016/0324785 A1    Nov. 10, 2016

(30) Foreign Application Priority Data
Jan. 3, 2014  (GB) .................................. 1400117.6

(51) Int. Cl.
*A61K 9/20* (2006.01)
*A61K 31/122* (2006.01)

(52) U.S. Cl.
CPC .......... *A61K 9/2018* (2013.01); *A61K 9/2013* (2013.01); *A61K 31/122* (2013.01)

(58) Field of Classification Search
CPC ... A61K 9/2018; A61K 31/122; A61K 9/2013
See application file for complete search history.

(56) References Cited

U.S. PATENT DOCUMENTS

2009/0060996 A1* 3/2009 Kristjansson ...... A61K 31/4365
424/465

FOREIGN PATENT DOCUMENTS

| CN | 102976948 A | 3/2013 |
| EP | 0591275 B1 | 4/1994 |
| WO | 93/00080 A1 | 1/1993 |
| WO | 2013181292 A1 | 12/2013 |

OTHER PUBLICATIONS

Clopidogrel_C16H16CINO2S—PubChem, retrieved Mar. 15, 2018 (Year: 2018).*
International Search Report for International Application No. PCT/GB2015/050006 (dated Mar. 18, 2015)(2 pages).

* cited by examiner

*Primary Examiner* — Sarah Pihonak
*Assistant Examiner* — Jason Deck
(74) *Attorney, Agent, or Firm* — Lucas & Mercanti, LLP

(57) ABSTRACT

The present invention relates to oral pharmaceutical compositions comprising nitisinone, or a pharmaceutically acceptable salt thereof, their use in the treatment of tyrosinemia, such as Hereditary Tyrosinemia type-1 (HT-1), or alkaptonuria. The compositions have improved stability characteristics. The invention also relates to processes for producing nitisinone.

7 Claims, 5 Drawing Sheets

PHARMACEUTICAL COMPOSITION

CROSS-REFERENCE TO RELATED APPLICATIONS

This application is a 371 of PCT/GB2015/050006 filed Jan. 5, 2015, which claims the benefit of United Kingdom Application 1400117.6, filed Jan. 3, 2014.

FIELD OF THE INVENTION

The present invention relates to a pharmaceutical composition. In particular, it concerns a pharmaceutical composition of nitisinone which possesses excellent storage stability.

BACKGROUND OF THE INVENTION

Nitisinone (IUPAC name: 2-[2-nitro-4-(trifluoromethyl) benzoyl] cyclohexane-1,3-dione) is currently approved under the trade name ORFADIN (FDA NDA NO21232) to treat Hereditary Tyrosinemia type-1 (HT-1). This is a rare genetic disorder in which the newborn child is unable to break down the amino acid tyrosine, which causes the build up of toxic metabolites that can lead to liver failure, kidney dysfunction and neurological problems. Daily treatment with nitisinone (dosage 1 mg/kg) prevents the build up of toxic metabolites.

Nitisinone has the structural formula:

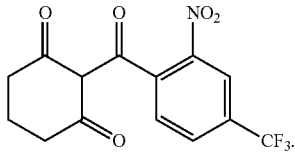 [SMILES: O=C1CCCC(=O)C1C(=O)c1ccc(C(F)(F)F)cc1[N+](=O)[O-]]

As the commercial product ORFADIN, nitisinone is currently administered orally in capsule form, available in three dosages, 2, 5 and 10 mg. It is an immediate release capsule formulation of nitisinone with pre-gelatinised starch as the only excipient.

However, one of the major disadvantages concerning the currently available commercial product is that, due to stability issues, it must be stored at 2-8° C. (i.e. it must be refrigerated). This is a significant drawback to HT-1 patients and their families. As a result, it is an object of the present invention to provide a nitisinone composition which is stable under a range of temperature conditions, such that there are no longer any storage implications. The benefit of such a formulation is that it will allow HT-1 patients to travel more freely and to gain more independence without the worry of keeping the medication within the required storage conditions.

SUMMARY OF THE INVENTION

Accordingly, in a first aspect of the invention, there is provided a pharmaceutical composition suitable for oral administration, wherein the composition is in the form of a compressed tablet and comprises nitisinone, or a pharmaceutically acceptable salt thereof, at least one saccharide, wherein the saccharide is a disaccharide or oligosaccharide, and at least one pharmaceutically acceptable excipient, provided that the composition does not contain magnesium stearate.

One of the main contributing factors to the instability of nitisinone at room temperature is its susceptibility to irreversibly form unwanted by-products. In particular, it has been shown that nitisinone is prone to forming cyclisation products at increased temperature. The cyclisation reaction, which is shown below, involves cyclisation of one of the carbonyl groups of the cyclohexanedione ring onto the phenyl ring, and loss of the nitro group.

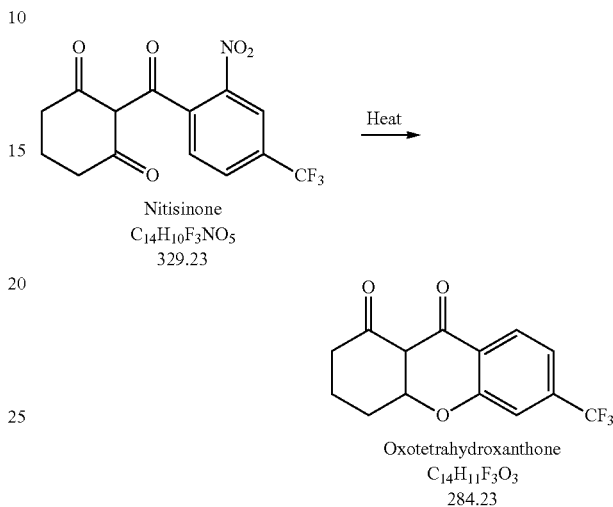

The cyclised impurity identified must not exceed the qualification threshold (i.e. below which toxicity testing is not required) of 0.15% w/w (with respect to the total amount of nitisinone) or 1.0 mg/day (whichever is lower) in accordance with ICH (International Conference on Harmonisation of Technical Requirements for Registration of Pharmaceuticals for Human Use) guidelines for drug substance impurities Q3A(R2), when limited to a maximum daily API dose of 2 g/day. For pharmaceutical compositions containing nitisinone, the impurity should not exceed a qualification threshold of 0.2% or 0.5% w/w (with respect to the total amount of nitisinone in the composition), depending on the dose of nitisinone to be administered.

Possible alternative nitisinone capsule and tablet compositions include those disclosed in EP0591275. These compositions typically contain a number of components, in particular the lubricant magnesium stearate. However, the inventors have found that the presence of magnesium stearate, and metal ions in general, renders the compositions unstable on storage under a range of temperature conditions. Surprisingly, tablet compositions which do not contain magnesium stearate are no longer prone to formation of the cyclised impurity associated with nitisinone, particularly during storage.

In a preferred embodiment of this aspect, the composition does not contain metal ions. In addition or alternatively, it is also preferable that the composition does not contain pre-gelatinised starch, and preferably it does not contain any starch. In a further embodiment of this aspect, the composition may also contain at least one saccharide and/or at least one fat. These additional components may further improve the stability of the present composition.

In a second aspect of the invention, there is provided a pharmaceutical composition suitable for oral administration, wherein the composition comprises nitisinone, or a pharmaceutically acceptable salt thereof, at least one saccharide, and at least one fat.

The composition of this aspect may be presented in any physical form. However, it is preferably provided as a compressed dosage form, such as a tablet. In tablet form, the composition of the invention has been shown to exhibit excellent stability under both accelerated and long-term conditions. In particular, very little or no cyclisation product is observed. The tablet form is also beneficial from the patient's perspective, making it easier to take the required medication.

In a third aspect of the invention, there is provided a pharmaceutical composition suitable for oral administration, the composition comprising nitisinone, or a pharmaceutically acceptable salt thereof, at least one saccharide, wherein the saccharide is a disaccharide or oligosaccharide, and at least one pharmaceutically acceptable excipient, provided that the composition does not contain magnesium stearate or starch. Preferably, the composition does not contain metal ions. As discussed herein, compositions containing magnesium stearate and/or starch have been shown to promote the formation of unwanted impurities (i.e. cyclised product) which breach regulatory guidelines for medicinal products.

The term 'pharmaceutically acceptable salt' as used herein refers to salts of nitisinone and includes salts with organic bases, salts with inorganic acids, salts with organic acids and salts with basic or acidic amino acids. Salts with acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R,3R)-2,3-dihydroxysuccinate salt, phosphate salt, sulphate salt, benzoate salt, 2-hydroxy-benzoate salt, S-(+)-mandelate salt, S-(−)-malate salt, S-(−) pyroglutamate salt, pyruvate salt, p-toluenesulfonate salt, 1-R-(−)-camphorsulfonate salt, fumarate salt and oxalate salt. The nitisinone used in the composition of the invention may be in either solvate (e.g. hydrate) or non-solvate (e.g. non-hydrate) form.

General methods for the preparation of salts are well known to the person skilled in the art. Pharmaceutical acceptability of salts will depend on a variety of factors, including formulation processing characteristics and in vivo behaviour, and the skilled person would readily be able to assess such factors having regard to the present disclosure.

In a preferred embodiment of the second aspect of the invention, the saccharide may be a monosaccharide, disaccharide or oligosaccharide. In the first aspect of the invention, one or more monosaccharides may also be present, in addition to the disaccharide or oligosaccharide.

Suitable monosaccharides include glucose (dextrose), fructose (levulose), galactose, ribose, arabinose, allose, fucose, altrose, mannitol, mannose, sorbitol and xylose. Suitable disaccharides include lactose, lactulose, sucrose, sucralose, trehalose, and robinose. Suitable oligosaccharides include saccharides comprising from 3 to 9 monosaccharides, preferably from 3 to 6 monosaccharides, or from 2 to 4 disaccharides, or appropriate combinations thereof.

In a preferred embodiment of the second aspect of the invention, the saccharide is a monosaccharide or disaccharide, such as mannitol, sorbitol, fructose or lactose, preferably fructose or lactose. Such saccharides function well as fillers in the composition of the invention and help to reduce the chemical lability of the nitisinone API, in particular the formation of the cyclised product. Most preferably, in relation to both the first and second aspects of the invention, the saccharide is a disaccharide, such as lactose (e.g. SuperTab® 30GR).

In a further preferred embodiment of the first and second aspects of the invention, the fat may be a monoglyceride, diglyceride or triglyceride, the fatty acid moieties of which are saturated or unsaturated, preferably saturated, and contain from 6 to 30 carbon atoms. More preferably, the fat is a diglyceride. Such fats provide beneficial properties as lubricants in the preparation of the composition of the invention (particularly where the composition is a tablet). Surprisingly, and in contrast to the lubricant magnesium stearate, these fats have been found to aid stability of the composition by preventing the formation of impurities in a similar manner to the saccharide component.

Preferably, the fatty acid moieties of the fat contain from 18 to 24 carbon atoms, more preferably from 20 to 22 carbon atoms. Furthermore, the fat of the composition is most preferably glycerol dibehenate (e.g. Compritol® 888). This material may provide even further enhanced stability to the composition, specifically in preventing the formation of the aforementioned cyclised product.

The term 'saturated' as used herein refers to fatty acid moieties containing only carbon-carbon single bonds, i.e. an alkyl group. The term 'unsaturated' as used herein refers to fatty acid moieties containing at least one carbon-carbon double or triple bond (i.e. an alkenyl group, —CH$_2$=CH$_2$—, or an alkynyl group, —CH≡CH—). Any alkenyl groups which may be present may exist in either cis or trans geometries. Preferably, the fatty acid moieties of the fat are either saturated, or unsaturated with one or more alkenyl groups.

In a particularly preferred embodiment of the invention, the saccharide is lactose and the fat is glycerol dibehenate. This combination of excipients has been shown to provide a composition which has evident stability in terms of long-term storage (e.g. no degradation of the drug substance), particularly in formulations comprising a compressed tablet.

The stability of the present pharmaceutical compositions is an important advantage of the invention. Accordingly, the pharmaceutical compositions of the invention may be characterised such that they have a stability (i.e. up to 0.5% nitisinone impurities, preferably up to 0.2% nitisinone impurities, in particular the cyclised impurity, as measured by HPLC under ICH guidelines) of at least 2 months at room temperature (e.g. 15 to 25° C.), preferably at least 4 months or 6 months, most preferably 12 months at room temperature.

Alternatively, the compositions may have a stability of at least 2 months at 25 to 50° C., preferably at least 4 months or 6 months, most preferably 12 months. In a preferred aspect, the compositions may exhibit a stability of at least 2 months under accelerated storage conditions of 40° C. and 75% relative humidity, preferably at least 4 months, and/or at least 2 months, preferably at least 4 months, under long-term storage conditions of 25° C. and 60% relative humidity. In addition or alternatively, the compositions may exhibit a stability of at least 2 months under intermediate conditions of 30° C. and 65% relative humidity, preferably at least 4 months or 6 months, most preferably 12 months. More preferably, the composition has a stability of at least 6 months, preferably at least 12 months, under accelerated conditions of 40° C. and 75% relative humidity, and/or at least 6 months, preferably at least 12 months, under long-term conditions of 25° C. and 60% relative humidity. Even more preferably, the composition has a stability such that substantially no increase in cyclised impurity is detectable by HPLC over a period of at least 2 months, preferably at least 4 or 6 months, even more preferably at least 12 months.

In determining the stability of the pharmaceutical compositions of the invention, the level of cyclised product may be determined by means of the HPLC method defined in the examples.

In another aspect, the invention provides the pharmaceutical composition according the invention, for use in therapy. In addition, there is provided the composition of the invention, for use in the treatment of tyrosinemia, such as Hereditary Tyrosinemia type-1 (HT-1), or alkaptonuria. Use in the treatment of Hereditary Tyrosinemia type-1 (HT-1) is most preferred.

In a fourth aspect of the invention, there is provided a process for producing nitisinone, wherein the process comprises extracting the nitisinone product under basic conditions, such as at a pH of 8 or more, preferably 9 or more, 10 or more, or 11 or more, more preferably 11 to 13, e.g. around 12. Surprisingly, it was found that when the extraction of the nitisinone product was conducted under these conditions, the yield was improved due to a reduction in degradation of the product in the work-up procedure. Similarly, the yield was improved when the process further comprised precipitating the nitisinone product via an acidification to a pH of approximately 2.

When the process proceeds via an O-acyl intermediate produced by the reaction of 1,3-cyclohexanedione with a base and 2-nitro-4-(trifluoromethyl)benzoyl chloride, it was also found that the yield could be improved by careful addition of a Lewis acid, preferably TMSCN (trimethylsilyl cyanide). Due to the long-term instability of the O-acyl intermediate, it is preferable that treatment of the O-acyl intermediate with the Lewis acid is commenced within around four hours of formation of the O-acyl intermediate. After four hours, the O-acyl intermediate begins to degrade.

In a fifth aspect of the invention, there is provided a process for producing a crystalline form of nitisinone, wherein the process comprises recrystallising a sample of nitisinone from an acetone:water solvent system. Preferably, the recrystallisation is carried out at a temperature of up to 50° C., more preferably up to 45° C. In addition, it is preferable that the recrystallisation is carried out using a ratio of acetone:water from 3:7 to 7:3, more preferably from 3:4 to 6:3.

BRIEF DESCRIPTION OF THE DRAWINGS

The invention will now be described in more detail by way of example only and with reference to the following figures.

DETAILED DESCRIPTION OF THE INVENTION

Examples

Example 1—Synthesis of Nitisinone

Figure 1A:
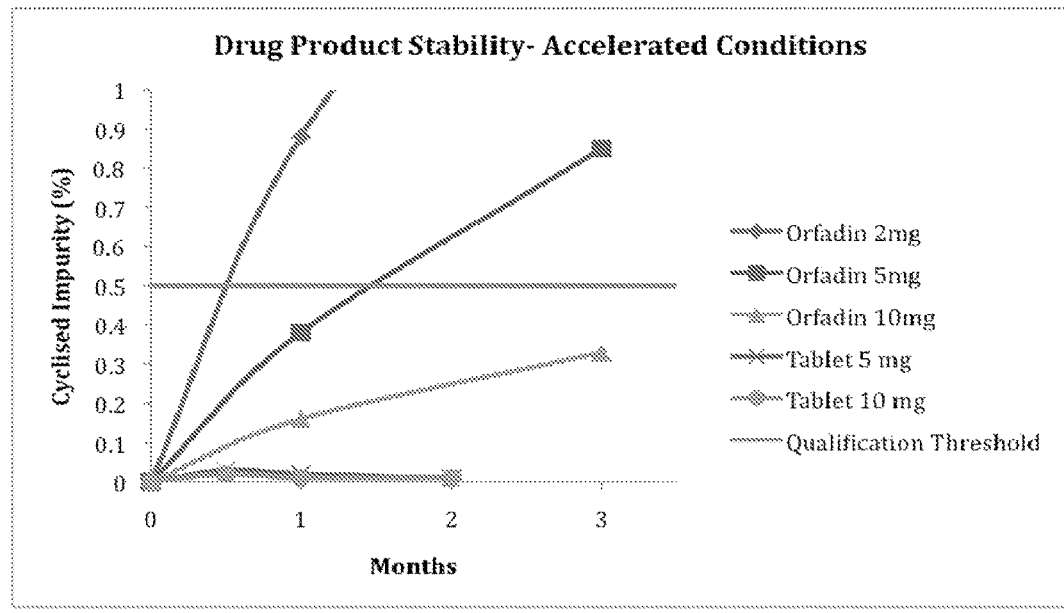
FIG. 1a shows drug stability data under accelerated conditions for ORFADIN and a tablet formulation according to the invention against a qualification threshold of 0.5%.
Figure 1B:
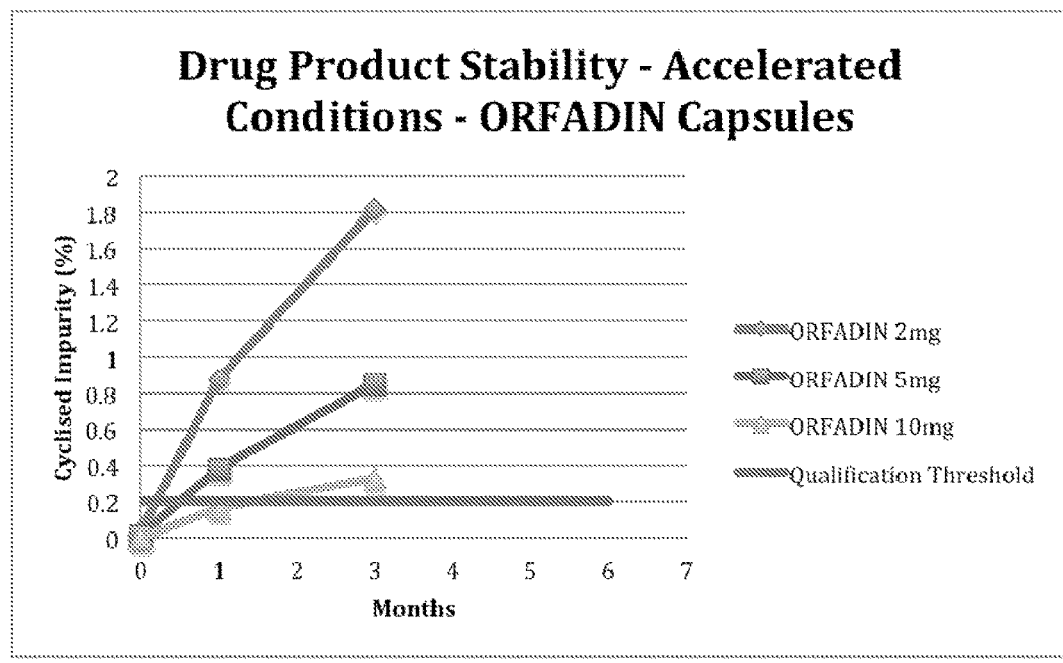
FIG. 1b shows drug stability data under accelerated conditions for ORFADIN against a qualification threshold of 0.2%.
Figure 1C:
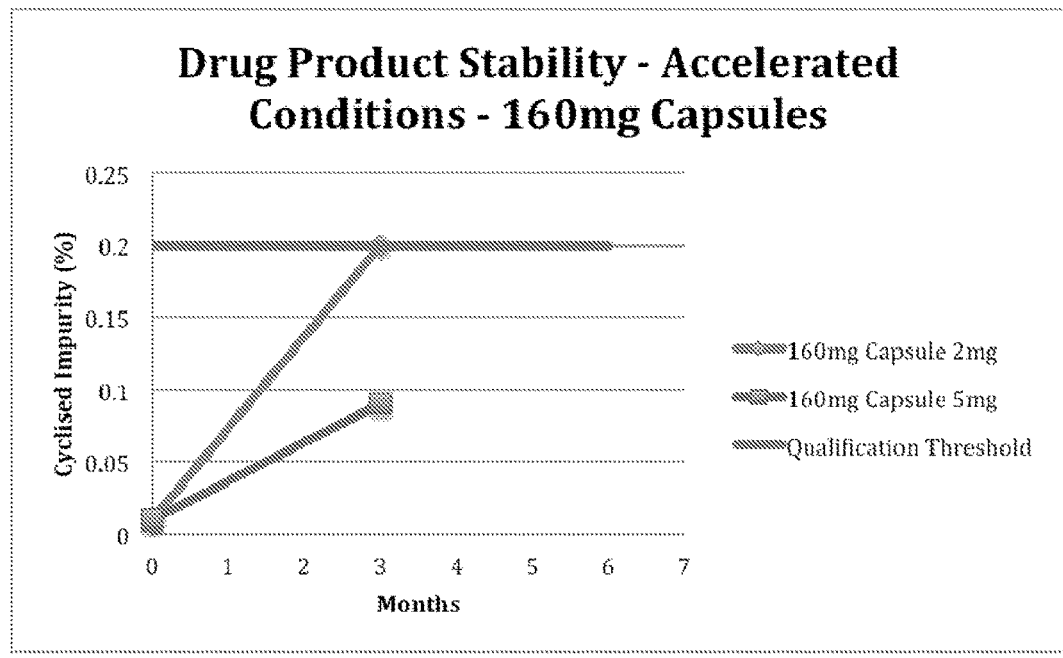
FIG. 1c shows drug stability data under accelerated conditions for a 160 mg lactose capsule formulation as described herein against a qualification threshold of 0.2%.
Figure 1D:
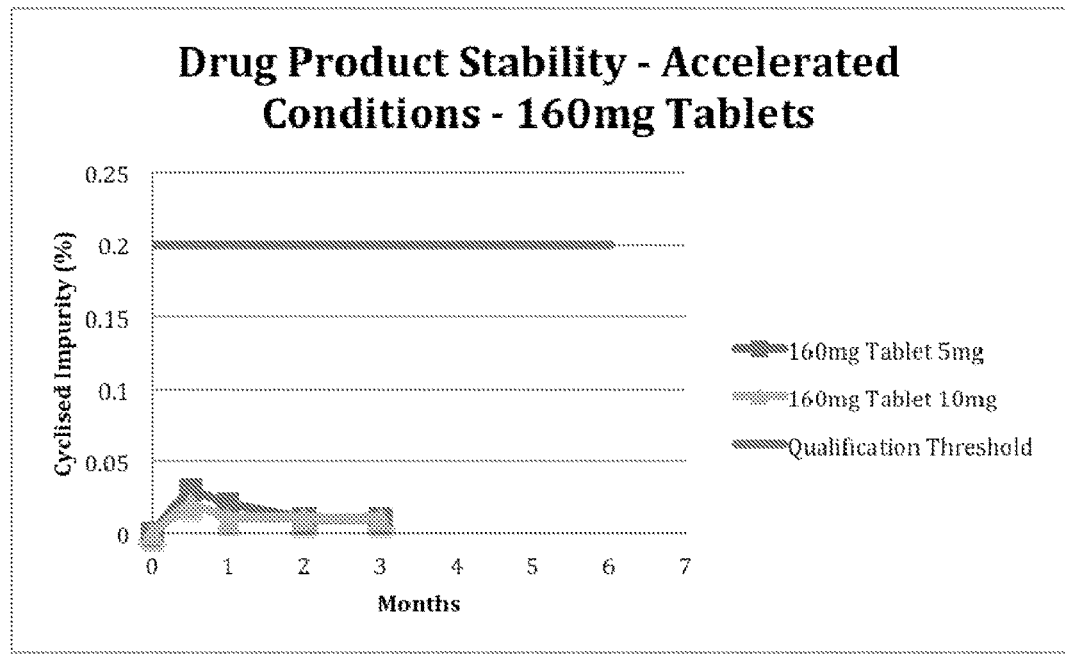
FIG. 1d shows drug stability data under accelerated conditions for a 160 mg tablet formulation according to the invention against a qualification threshold of 0.2%.
Figure 1E:
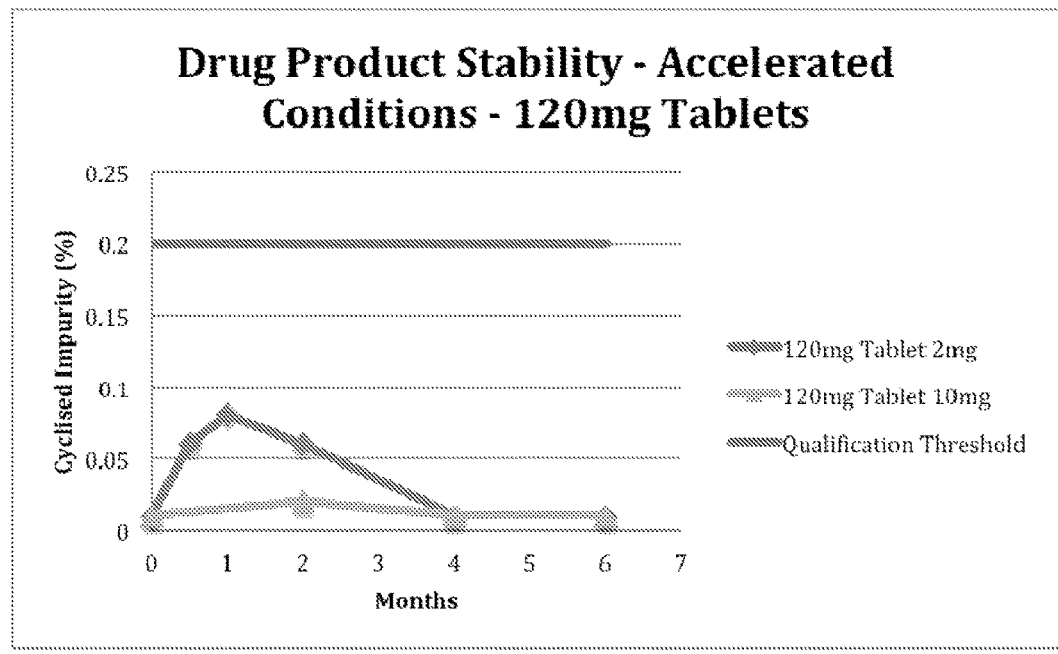
FIG. 1e shows drug stability data under accelerated conditions for a 120 mg tablet formulation according to the invention against a qualification threshold of 0.2%.

The synthesis of nitisinone is outlined in the scheme below. In particular, adaptations to stage 1, especially the extraction and precipitation steps, and the timing of the treatment of the O-acyl intermediate with TMSCN, improved the yield from less than 50% to more than 85%, and maintained a purity of greater than 95% (compared to the route described in U.S. Pat. No. 5,550,165). Changing the solvent used for the recrystallisation of the product from ethyl acetate, as also described in U.S. Pat. No. 5,550,165, to acetone/water improved yields from 37% to greater than 90%, whilst maintaining a purity of greater than 99.9%. The added advantage of using such solvents for the recrystallisation is that they conform to ICH guidelines for residual solvent levels.

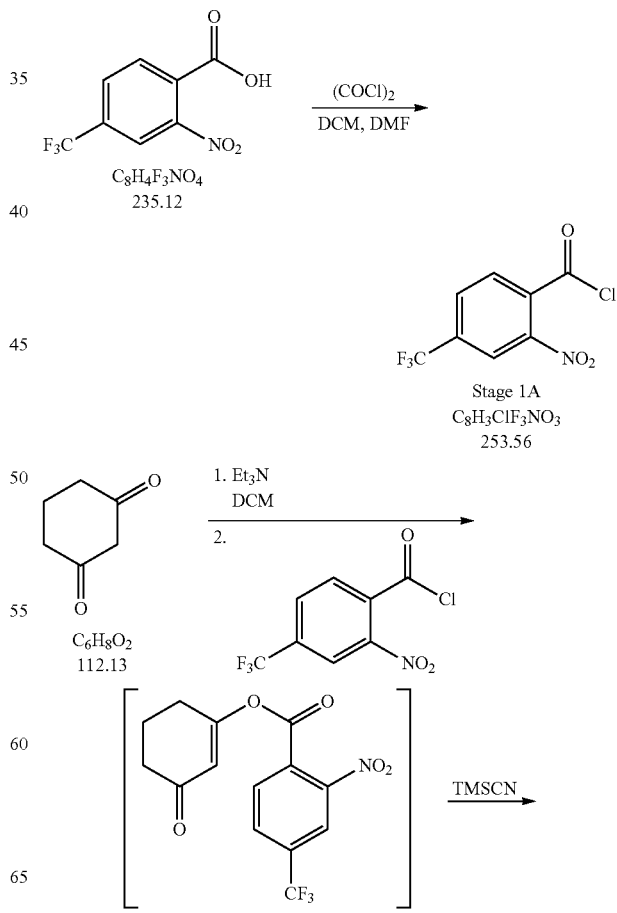

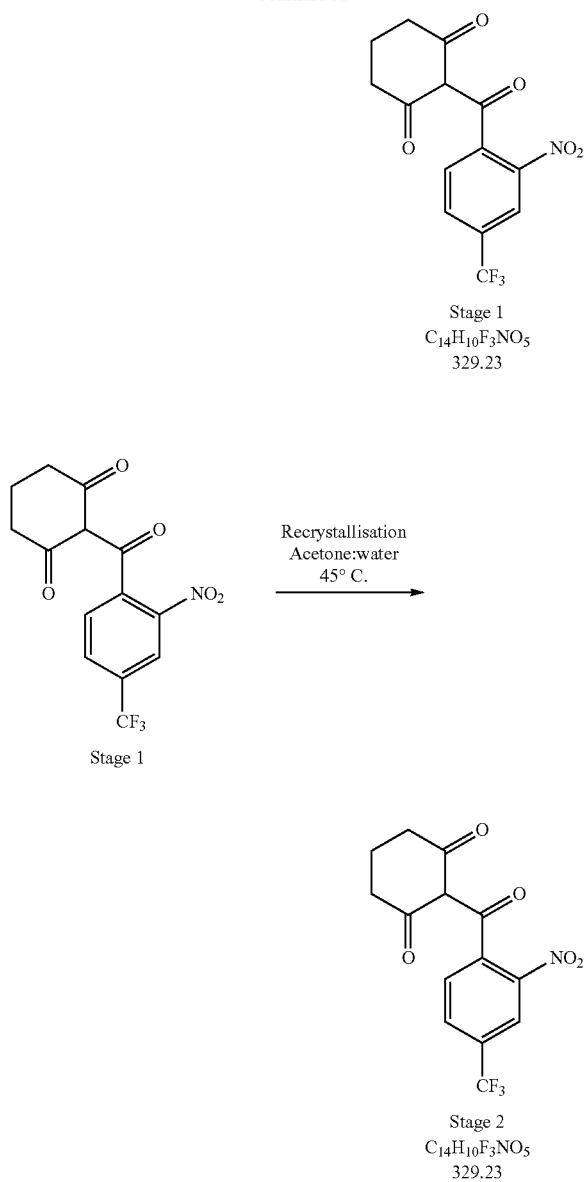

Stage 1
$C_{14}H_{10}F_3NO_5$
329.23

Stage 2
$C_{14}H_{10}F_3NO_5$
329.23

In the general procedure, 2-Nitro-4-(trifluoromethyl) benzoic acid was converted to the corresponding acid chloride via addition of 1.03 equivalents of oxalyl chloride in dichloromethane. 1,3-Cyclohexanedione was converted to the enol via addition of 3.0 equivalents of triethylamine followed by addition of the previously prepared acid chloride. Catalytic trimethylsilyl cyanide, TMSCN, (0.05 equivalents) was added and the reaction stirred overnight. The reaction was washed with 2M hydrochloric acid, extracted into 1M sodium hydroxide at pH-12, acidified to pH-2, extracted into isopropylacetate and crystallised to give Nitisinone.

Process Improvement

While the purity of the samples was high (99.4-99.6%), the overall yield of stage 1 was extremely low 28-50%. To further understand the reaction and to determine where material was being lost, studies were undertaken to investigate the stability of the O-acyl intermediate and Nitisinone under stage 1 conditions (Table 1).

TABLE 1

Stability of the O-acyl intermediate[a]

| Time h | Acid Cl %[b] | Subst BA % | Intermediate % | Nitisinone % |
|---|---|---|---|---|
| 2 | 69 | 12 | 18 | 0.0 |
| 3.5 | 44 | 12 | 38 | 0.0 |
| 6 | 45 | 16 | 26 | 0.0 |
| 7 | | TMSCN addition | | |
| 24 | 0.0 | 16.0 | 0.0 | 62.0 |
| After workup | 0.0 | 0.61 | 0.0 | 99.39 |

[a]Initial HPLC method and original workup;
[b]Calculated from reference standard of the methyl ester; Acid Cl = acid chloride; BA = benzoic acid; Intermediate = O-acyl intermediate.

Results indicated that the O-acyl intermediate is unstable and starts to degrade after 4 hours (Table 1 entries 3.5 h and 6 h). TMSCN was therefore added after seven hours and the reaction left overnight. No intermediate was observed after twenty four hours or after workup and recrystallisation from isopropylacetate. Due to the instability of the O-acyl intermediate, TMSCN addition should occur before four hours has elapsed. Further experiments showed that the addition can occur after only twenty minutes with no detrimental effects on the yield or purity. To study the stability of Nitisinone, addition of TMSCN after twenty minutes and subsequent monitoring showed that the formation of Nitisinone is complete within 2 h and stable to overnight stir out.

Due to the high percentage of Nitisinone before the workup and the low yield observed for stage 1, losses in the workup and recrystallisation from isopropylacetate were investigated. In an attempt to improve the yield and avoid an unnecessary recrystallisation, the solution was acidified to pH 2 and the resulting precipitate was filtered, washed with water and dried in a vac oven at 40° C. (Table 2). A significant increase in yield was observed (30% to 90%). Calculations had shown that on scale up acidification using 2 M hydrochloric acid gave a process with poor volumetrics (i.e. low batch size/vessel volume), therefore in an attempt to reduce the volumetrics of the work-up, acidification to pH-2 was a carried out using concentrated 36% hydrochloric acid (Table 2, batch 9). No loss of yield or purity was observed and ~$\frac{1}{10}^{th}$ of the volume of acid was required.

TABLE 2

Results from revised workup conditions

| Batch (scale) | Yield (g, %) | Nitisinone % | Subst BA % |
|---|---|---|---|
| 5 (10 g) | 12.54   90 | 98.45 | 1.28 |
| 6 (20 g) | 23.00   82 | 97.64 | 2.24 |
| 7[a] (50 g) | 63.00   90 | 95.00 | 2.30 |
| 8 (50 g) | 63.50   91 | 98.40 | 1.23 |
| 9[b] (20 g) | 23.80   85 | 97.04 | 2.93 |

[a]Result from excess addition of oxalyl chloride;
[b]Result using conc HCl in work-up; BA = benzoic acid.

A range of solvents were screened for suitable recrystallisation conditions (Table 3).

TABLE 3

Recrystallisation solvent study for stage 2

| Solvent (Vols) | Nitisinone % | Subst BA % | Yield % | Notes |
|---|---|---|---|---|
| Input material | 98.45 | 1.28 | 90 | — |
| EtOAc (7.5) | 99.90 | 0.10 | 37 | |
| EtOAc/Hexane (10) | 99.96 | 0.04 | 66 | |

TABLE 3-continued

Recrystallisation solvent study for stage 2

| Solvent (Vols) | Nitisinone % | Subst BA % | Yield % | Notes |
|---|---|---|---|---|
| Toluene (9) | 99.95 | 0.05 | 40 | |
| Hexane (15) | 98.39 | 1.49 | 95 | Reslurry |
| Input material | 97.64 | 2.24 | 90 | — |
| EtOH (10) | 99.46 | 0.54 | 90 | Reslurry |
| IPA (10) | 99.43 | 0.55 | 84 | Reslurry |
| Heptane (10) | 97.81 | 2.11 | 86 | Reslurry |
| Acetone (10) | — | — | — | Dissolved at RT |
| Acetone (4) | — | — | — | Slow recryst |
| Acetone:Heptane (3:3) | 99.92 | 0.08 | 68 | |
| iPrOAc:Heptane (7:10) | 100.00 | 0.00 | 78 | |
| EtOAc:Heptane (6:6) | 100.00 | 0.00 | 66 | |
| Acetone/water (3:4) | 99.91 | 0.09 | 94 | |
| Acetone/water (8:4) | 99.94 | 0.06 | 96 | RT (14° C.) |
| Aqueous acid/base | 99.36 | 0.61 | 82 | |
| Input material | 98.40 | 1.23 | 90 | — |
| Acetone/water (7:3) | 99.97 | 0.03 | 86 | 20 g, 22° C. |
| Acetone/water (6:3) | 99.98 | 0.02 | 91 | 20 g, 35° C. |
| Acetone:wate (4:3) | 99.95 | 0.05 | 90 | 20 g, 45° C. |

BA = benzoic acid.

The recrystallisation temperatures did not exceed 45° C. as a precaution. Stage 1 was dissolved in the minimum amount of solvent with heating to 45° C., stirred for ten minutes, co-solvent added if required, stirred for a further 20 minutes at 45° C., cooled to 0° C., stirred for 30 minutes and filtered. Recrystallisation from acetone/water was shown to give the best purity to yield ratio and in a suitable volume of solvent (94% yield, 99.9% purity from seven volumes of solvent). These conditions were further investigated on a larger scale and at various temperatures to determine solvent volume ratios. Acetone/water at 45° C. was chosen as the final recrystallisation conditions as it requires the least volumes of solvent and provides material in good yield and purity.

It is a requirement of GMP manufacturing that the final recrystallisation includes a filtration through a polishing filter to remove particulates, and so the GMP process would involve filtration of the hot acetone solution. This means that it is likely that the solution of Nitisinone in acetone at 45° C. could be held at elevated temperature for a prolonged period of time. The stability of stage 1 at 45° C. was tested over a 6 hour period to confirm that the Nitisinone would not degrade under these conditions (Table 4). No loss of purity was observed. Therefore, acetone could be used in the hot filtration step of the GMP process.

TABLE 4

Stage 1 stability in acetone

| Time h | Nitisinone % | Subst BA % |
|---|---|---|
| 0.0 | 97.64 | 2.24 |
| 0.5 | 97.63 | 2.24 |
| 1.5 | 97.65 | 2.21 |
| 2.5 | 97.65 | 2.23 |
| 3.5 | 97.64 | 2.21 |
| 4.5 | 97.65 | 2.21 |
| 5.5 | 97.66 | 2.20 |

BA = benzoic acid.

Final recrystallisation conditions: Stage 1 dissolved in acetone (4×stage 1 charge in ml) with heating to 45° C. and stirred for ten minutes, water (3×stage 1 charge in ml) added dropwise and the resulting slurry stirred for a further 20 minutes at 45° C., cooled to 0° C., stirred for 30 minutes and filtered.

The final recrystallisation is also excellent for purging remaining substituted benzoic acid to very low levels.

On scale-up, drying from water can often take much longer than on lab scale and could potentially result in degradation of the product, especially with a product that could potentially be prone to hydrolysis. Following filtration of Nitisinone from the final recrystallisation, the filter-cake was washed with water to remove the residual mother liquors. Due to its high solubility in acetone and other organic solvents, a solvent wash was not appropriate as high yield losses would likely be incurred. A water wash also helped remove residual inorganics. Drying studies were therefore carried out to determine the stability of the recrystallised material and try to ensure that there would be no unexpected degradation during the drying phase of the scale-up manufacture (Table 5).

TABLE 5

Stage 2 drying studies

| Entry | Time/h | Nitisinone % | Subst BA % | KF % |
|---|---|---|---|---|
| 1 | 0 | 100 | 0.00 | 18.45 |
| 2 | 4 | 99.97 | 0.03 | 0.39 |
| 3 | 7 | 99.95 | 0.05 | 0.37 |
| 4 | 24 | 99.97 | 0.03 | 0.19 |
| 5 | 60 | 99.97 | 0.05 | 0.12 |
| 6 | 0 | 100 | 0.00 | 34.45 |
| 7 | 4 | 99.94 | 0.06 | 0.44 |
| 8 | 7 | 99.92 | 0.08 | 0.16 |
| 9 | 24 | 99.94 | 0.06 | 0.11 |
| 10 | 60 | 99.95 | 0.05 | 0.18 |
| 11[a] | 0 | 99.97 | 0.03 | — |
| 12[a] | 24 | 99.98 | 0.02 | — |
| 13[a] | 60 | 100 | 0.00 | — |
| 14 | 0 | 99.97 | 0.03 | 0.12 |
| 15 | 24 | 99.91 | 0.09 | — |
| 16 | 48 | 99.87 | 0.04 | — |
| 17 | 72 | 99.99 | 0.01 | — |
| 18 | 96 | 99.97 | 0.03 | — |
| 19 | 168 | 99.98 | 0.02 | — |

[a]Saturated sample heated at 40° C., no vacuum;
BA = benzoic acid; KF = water content determined by Karl Fischer titration.

Two separate batches were heated over a 60 hour period with purity and KF values taken (entries 1-10). Both batches showed that the recrystallised Nitisinone was stable for extended periods of drying with little to no loss in purity (any changes are thought to be within experimental error). A sample of Nitisinone was suspended in water and heated at 40° C. with no vacuum for 60 hours (entries 11-13), to simulate poor drying. No loss of purity was observed confirming the stability of Nitisinone in water. A second sample was wetted each morning and dried under vacuum overnight to study the effect of repeatedly wetting and drying the sample (entries 14-19). An unexpected unknown impurity was observed in the 48 h sample but this can be attributed to a column impurity as it had never been observed before or since (even for the same sample). Acetone/water has been shown to be a viable recrystallisation solvent system with the resulting product stable to extended periods of drying, even from water.

The complete synthesis process was found to be repeatable on a large scale, up to 120 g, producing material in high yield (80%) with a purity of 99.97%.

Example 2—Stability Study

An API stability study showed that nitisinone prepared by the above synthetic procedure was stable with respect to cyclised impurity concentrations, staying within ICH limits at both long term (25° C./60% RH) and accelerated storage conditions (40° C./75% RH). Indeed, no formation of the aforementioned cyclised impurity was observed in the API. However, the ORFADIN capsules were not stable at the long-term or accelerated storage conditions, showing accelerated cyclised impurity formation compared to the nitisinone API alone, implying that reaction between the nitisinone API and the pre-gelatinised starch excipient is causing the impurity formation.

Data provided by the stability testing programme was conducted with the substance under investigation stored in the actual packaging used for storage and distribution. This was to determine if the substance remained compliant with the ICH specification criteria when tested over the period of its shelf life plus one year.

A sample of approximately 150 g of substance was used for the testing programme, with individual samples being approximately 7 g in size. The test was designed to simulate the product package, i.e. the sample was packed in a polythene bag, sealed and then placed inside another polythene bag liner. The sample was then held in a fibreboard cask with a fibreboard lid.

The sample was stored in an incubator maintained at 25° C.±2° C./60%±5% relative humidity (RH), and 40° C.±2° C./75%±5% RH.

After testing of an initial sample, a sample was tested at certain time intervals (Table 6), i.e. monthly (0 m, 1 m, 2 m, etc.).

The prepared API showed no deviation from specification under both accelerated and long-term storage conditions. There was no decrease in purity and the cyclised impurity remained below the identification threshold (0.10%) throughout the stability testing (measured by HPLC).

TABLE 6

| Stability of API over time | | | | | |
|---|---|---|---|---|---|
| Conditions | 0 m | 1 m | 2 m | 3 m | 6 m |
| 25° C./60% RH | 99.90% w/w | 99.87% w/w | 99.88% w/w | 99.91% w/w | 99.91% w/w |
| 40° C./75% RH | 99.90% w/w | 99.89% w/w | 99.88% w/w | 99.92% w/w | 99.96% w/w |

Example 3—Composition Compatibility

In order to identify suitable excipients to develop a temperature stable formulation, 4 standard fillers and 5 lubricants were mixed with nitisinone and stored under accelerated conditions for 1 week and 3 weeks. 10 preparations for each excipient were prepared by weighing approximately 10 mg of nitisinone and 500 mg of the excipient into a glass vial and mixing together by gentle swirling. To 5 lots of preparations, 50 µl of water was added to wet the sample. For a control, 10 preparations of the drug substance were prepared by weighing approximately 10 mg nitisinone into a suitable glass vial and to 5 lots of preparations, 50 µl of water was added to wet the sample.

HPLC analysis was used to quantify the relative amount of the cyclised impurity (RRT 0.7) for each formulation at each time point (Tables 7 and 8).

TABLE 7

| Effect of Lubricant | | | | | |
|---|---|---|---|---|---|
| Description | Cyclised Impurity - RRT 0.7 (norm %) | | | | |
| Analytical Method | HPLC | | | | |
| Excipients | Lubricants | | | | |
| 40° C./75% RH | | Glycerol Dibehenate | Croscarmellose Sodium | Magnesium Stearate | Sodium Starch Glycolate | Sodium Stearyl Fumurate |
| Initial | | 0.01 | 0.04 | 0.06 | 0.03 | 0.04 |
| 1 week | Wet | 0.03 | 0.29 | 0.24 | 0.15 | 0.20 |
|  | Dry | 0.02 | 0.44 | 0.15 | 0.09 | 0.16 |
| 3 weeks | Wet | 0.04 | — | — | 0.48 | 0.34 |
|  | Dry | 0.05 | — | — | 0.27 | 0.24 |

TABLE 8

| Effect of Filler | | | | | |
|---|---|---|---|---|---|
| Description | Cyclised Impurity - RRT 0.7 (norm %) | | | | |
| Analytical Method | HPLC | | | | |
| Excipients | Fillers | | | | API |
| 40° C./75% RH | Lactose | Microcrystalline Cellulose | Silicon Dioxide | Pre-gelatinised Starch | Nitisinone |
| Initial | 0.01 | 0.01 | 0.01 | 0.01 | 0.01 |
| 1 week Wet | 0.03 | 0.08 | 0.15 | 0.27 | 0.07 |
| Dry | 0.05 | 0.06 | 0.09 | 0.18 | 0.02 |
| 3 weeks Wet | 0.03 | 0.22 | 0.40 | 0.70 | 0.20 |
| Dry | 0.16 | 0.54 | 0.30 | 0.60 | 0.13 |

The excipient compatibility showed that the metal ion (magnesium or sodium) containing lubricants accelerated the formation of the cyclised impurity relative to the API only sample, whilst glycerol dibehenate slowed the impurity formation significantly.

A number of fillers also accelerated the formation of the cyclised impurity, notably and most significantly pre-gelatinised starch, which is currently used in the approved ORFADIN capsule formulation. The use of lactose did not promote the formation of the cyclised impurity.

Example 4—Tablet Formulations

Immediate release tablet formulations of nitisinone were developed in the same dose strengths as ORFADIN (Tables 9a and 9b).

TABLE 9a

Tablet formulation (160 mg)

| Name of Ingredient | Tablet Strength | | |
|---|---|---|---|
| | 2 mg tablets (amount/tablet) | 5 mg tablets (amount/tablet) | 10 mg tablets (amount/tablet) |
| Nitisinone | 2 mg | 5 mg | 10 mg |
| Glycerol Dibehenate | 4.8 mg | 4.8 mg | 4.8 mg |
| Lactose | 153.2 mg | 150.2 mg | 145.2 mg |
| Tablet weight | 160 mg | 160 mg | 160 mg |
| Tablet Diameter | | 7 mm | |
| Tablet Thickness | | 4 mm | |

The excipients and active pharmaceutical ingredient (API) were passed through a 500 μm screen before blending in a turbular blender (30 minutes at 30 rpm). The tablets were then compressed to a hardness of around 3KP (2.5-3.5) using standard curvature 7 mm round tooling. The tablets had a final weight of 160 mg.

TABLE 9B

Tablet formulation (120 mg)

| Name of Ingredient | Tablet Strength | | |
|---|---|---|---|
| | 2 mg tablets (amount/tablet) | 5 mg tablets (amount/tablet) | 10 mg tablets (amount/tablet) |
| Nitisinone | 2 mg | 5 mg | 10 mg |
| Glycerol Dibehenate | 1.6 mg | 1.6 mg | 1.6 mg |
| Lactose | 116.4 mg | 113.4 mg | 108.4 mg |
| Tablet weight | 120 mg | 120 mg | 120 mg |
| Tablet Diameter | | 7 mm | |
| Tablet Thickness | | 3 mm | |

The excipients and active pharmaceutical ingredient (API) were passed through a 400 μm screen before blending. The tablets were then compressed to a hardness of around 5.5KP (5-6) using standard curvature 7 mm round tooling. The tablets had a final weight of 120 mg.

Glycerol dibehenate, in the form of Compritol 888, is a registered GRAS substance with no upper acceptable daily intake (ADI) limit. The amount of glycerol dibehenate used in the formulation is within the amounts previously used in other formulations listed in the FDA inactive ingredients guide (up to 60 mg/dose).

Tablets (or capsules) of the composition may be contained in high density polyethylene (HDPE) bottles. No desiccant is required in the bottles containing the composition of the invention, since an excipient compatibility study showed that higher water content increased the stability of the product.

In particular, the formulation was developed to stay within specifications under accelerated storage conditions for a period of at least 6 months, which then allowed extrapolation of data from stability testing at the long-term conditions to demonstrate room temperature storage of the drug formulation product. At all stages, the new formulation was directly compared to the commercially available drug product, ORFADIN.

Example 5—Capsule vs Tablet Formulation vs ORFADIN

A capsule formulation was developed for comparison to the tablet formulation of the same excipient blend, as shown in the table below (Table 10), in order to determine the influence of dose form on stability.

TABLE 10

Capsule formulation

| Name of Ingredient | Capsule Strength | |
|---|---|---|
| | 2 mg capsules (amount/capsule) | 5 mg capsules (amount/capsule) |
| Nitisinone | 2 mg | 5 mg |
| Glycerol Dibehenate | 3.2 mg | 3.2 mg |
| Lactose | 154.8 mg | 151.8 mg |
| Fill weight | 160 mg | 160 mg |
| Size 3 HPMC Capsule | 1 Unit | 1 Unit |

The excipients and API were passed through a 1000 μm screen before blending in a turbular blender (30 minutes at 30 rpm). Following blending, 160 mg of the blend is placed into size 3 HPMC capsules using an automated encapsulation machine (Bonapace In-cap).

All three drug formulations (ORFADIN, capsule and tablet) underwent stability testing at the long term (25° C.±2° C./60%±5% RH) and accelerated (40° C.±2° C./75%±5% RH) storage conditions. At each time point, the drug product was compared to specification by the following methods: assay (mg nitisinone), related substances, and dissolution.

For each of the nitisinone formulations in question (ORFADIN, capsule and tablet), the only property found to change with time was the increase in the amount of the cyclised impurity (and the reduction in nitisinone). This was identified in the total related substance HPLC analytical method at a retention time of 0.7. Thus, the stability of each formulation and the subsequent comparisons were conducted based on only the amount of the cyclised impurity (RRT 0.7).

The stability data results for the accelerated and long-term conditions are summarised in Table 11 and Table 12, respectively.

TABLE 11

Impurity analysis under accelerated conditions
Storage Conditions: 40° C./75% RH
Analytical method: HPLC
Cyclised impurity: (RRT 0.7) NMT 0.5%

| | Formulation | | | | | | | | |
|---|---|---|---|---|---|---|---|---|---|
| | ORFADIN capsule pre-gelatinised starch formulation | | | Capsule lactose formulation | | | Tablet lactose formulation | | |
| Weight | | | | 160 mg | | | 160 mg | 120 mg | |
| Strength | 2 mg | 5 mg | 10 mg | 2 mg | 5 mg | 5 mg | 10 mg | 2 mg | 10 mg |
| Initial | 0.03 | 0.01 | ND | 0.01 | 0.01 | ND | ND | 0.01 | 0.01 |

TABLE 11-continued

Impurity analysis under accelerated conditions
Storage Conditions: 40° C./75% RH
Analytical method: HPLC
Cyclised impurity: (RRT 0.7) NMT 0.5%

| | Formulation | | | | | | | | |
|---|---|---|---|---|---|---|---|---|---|
| | ORFADIN capsule pre-gelatinised starch formulation | | | Capsule lactose formulation | | Tablet lactose formulation | | | |
| 2 weeks | | | | | | 0.03 | 0.02 | 0.06 | |
| 1 month | 0.88 | 0.38 | 0.16 | 0.20 | 0.09 | 0.02 | 0.01 | 0.08 | |
| 2 months | | | | | | 0.01 | 0.01 | 0.06 | 0.02 |
| 3 months | 1.82 | 0.85 | 0.33 | | | 0.01 | 0.01 | | |
| 4 months | | | | | | | | 0.01 | 0.01 |
| 6 months | | | | | | | | | |

NMT = not more than; RRT = relative retention time, relative to nitisinone.

TABLE 12

Impurity analysis under long-term conditions
Storage Conditions: 25° C./60% RH
Analytical method: HPLC
Cyclised impurity: RRT 0.7 (norm %)

| | Formulation | | | | | | |
|---|---|---|---|---|---|---|---|
| | ORFADIN capsule pre-gelatinised starch formulation | | | Capsule lactose formulation | | Tablet lactose formulation | |
| Weight | | | | 160 mg | | 160 mg | |
| Strength | 2 mg | 5 mg | 10 mg | 2 mg | 5 mg | 5 mg | 10 mg |
| Initial | 0.03 | 0.01 | ND | 0.01 | 0.01 | ND | ND |
| 2 weeks | | | | | | 0.01 | 0.01 |
| 1 month | 0.08 | 0.03 | 0.02 | 0.03 | 0.01 | 0.01 | 0.01 |
| 2 months | | | | | | 0.01 | 0.01 |
| 3 months | 0.15 | 0.05 | 0.03 | | | | |
| 6 months | 0.35 | 0.16 | 0.05 | | | | |
| 9 months | | | | | | 0.03 | 0.02 |
| 12 months | | | | | | 0.06 | 0.03 |

Accelerated Conditions

The results from the accelerated storage conditions are shown in Table 11 and FIGS. 1a-1e.

The amount of cyclised impurity within ORFADIN 2 mg and 5 mg capsules was found to be above the qualification threshold of 0.5% within 3 months at accelerated conditions, and the 10 mg capsules are projected to breach this threshold within 6 months. For the more stringent qualification threshold of 0.2%, the amount of cyclised impurity within ORFADIN 2 mg and 5 mg capsules was found to be above the qualification threshold within 1 month at accelerated conditions, and within 3 months for the 10 mg capsules. See FIG. 1b.

The lactose capsule formulation showed significant improvements in stability when compared to ORFADIN; however, projections demonstrated that the amount of cyclised impurity would breach the qualification threshold of 0.5% within 6 months for the 2 mg capsules. For the 0.2% qualification threshold, the amount of cyclised impurity would breach the qualification threshold at 1 month for the 2 mg capsules. See FIG. 1c.

The lactose tablet formulation showed no increase in the amount of cyclised impurity within the first 2 months, demonstrating high stability even at the accelerated conditions, and is thus projected not to breach the qualification threshold of 0.5% within 6 months. For the 0.2% qualification threshold, no increase in the amount of cyclised impurity was seen within the first 4 months, and is thus projected not to breach the qualification threshold within 6 months. See FIGS. 1d and 1e.

Long-Term Conditions

Figure 2A:
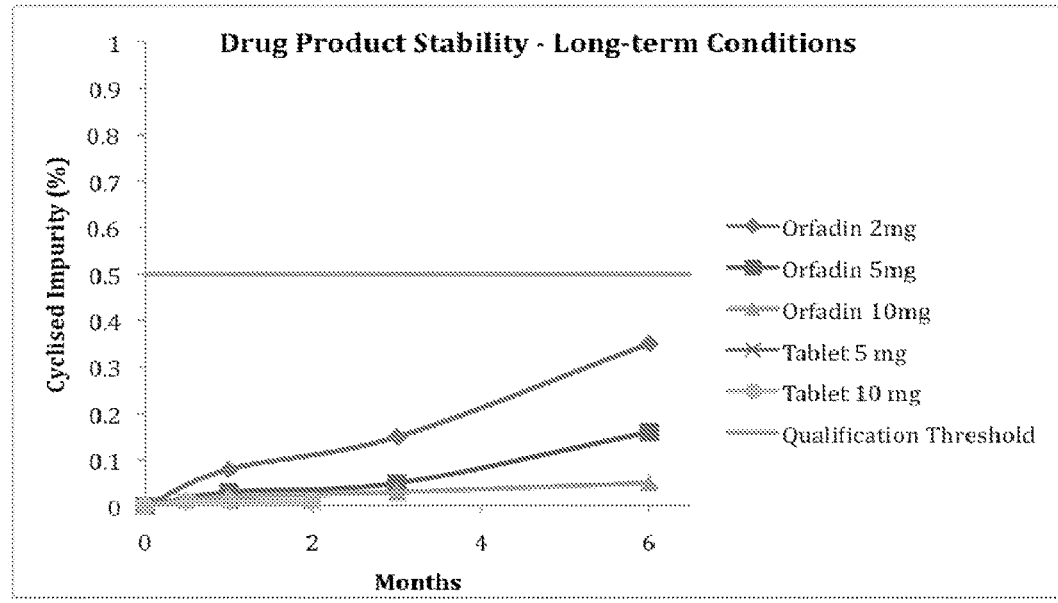
FIG. 2a shows drug stability data under long-term conditions for ORFADIN and a tablet formulation according to the invention against a qualification threshold of 0.5%.
Figure 2B:
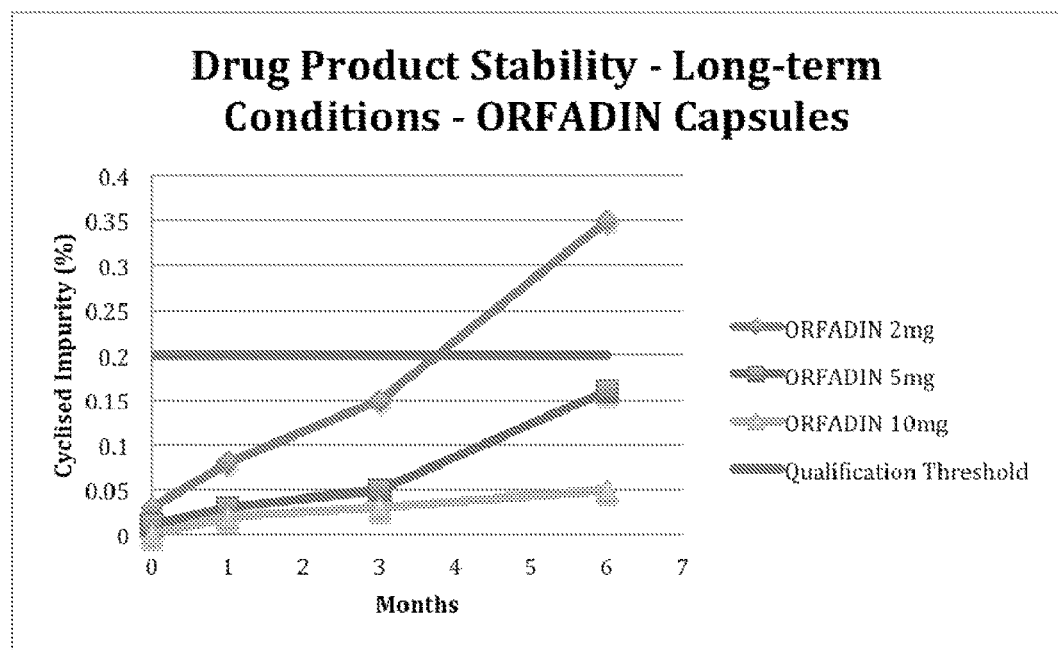
FIG. 2b shows drug stability data under long-term conditions for ORFADIN against a qualification threshold of 0.2%.
Figure 2C:
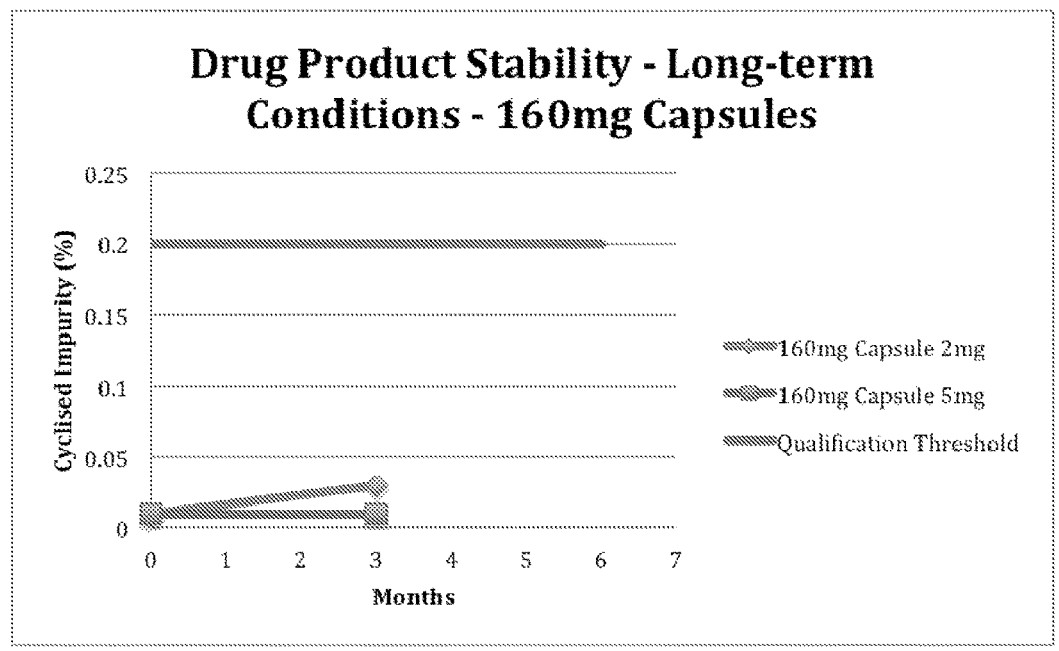
FIG. 2c shows drug stability data under long-term conditions for a 160 mg lactose capsule formulation as described herein against a qualification threshold of 0.2%.

The results from the accelerated storage conditions are shown in Table 12 and FIGS. 2a-c.

For ORFADIN, whilst the amount of cyclised impurity stayed below the qualification threshold of 0.5%, the rate of formation appeared to be accelerating. Extrapolating the rate of formation from months 3 to 6, the 2 mg capsule is projected to breach the qualification threshold of 0.5% within 12 months. The 5 mg and 10 mg capsules are expected to stay within the 0.5% qualification threshold in 12 months. For the 0.2% qualification threshold, the 2 mg capsule exceeded the threshold within 6 months. Extrapolating the rate of formation from months 3 to 6, the 5 mg capsule is projected to breach the qualification threshold of 0.2% within 12 months. The 10 mg capsules are expected to stay within the 0.2% qualification threshold in 12 months. See FIG. 2b.

Figure 2D:
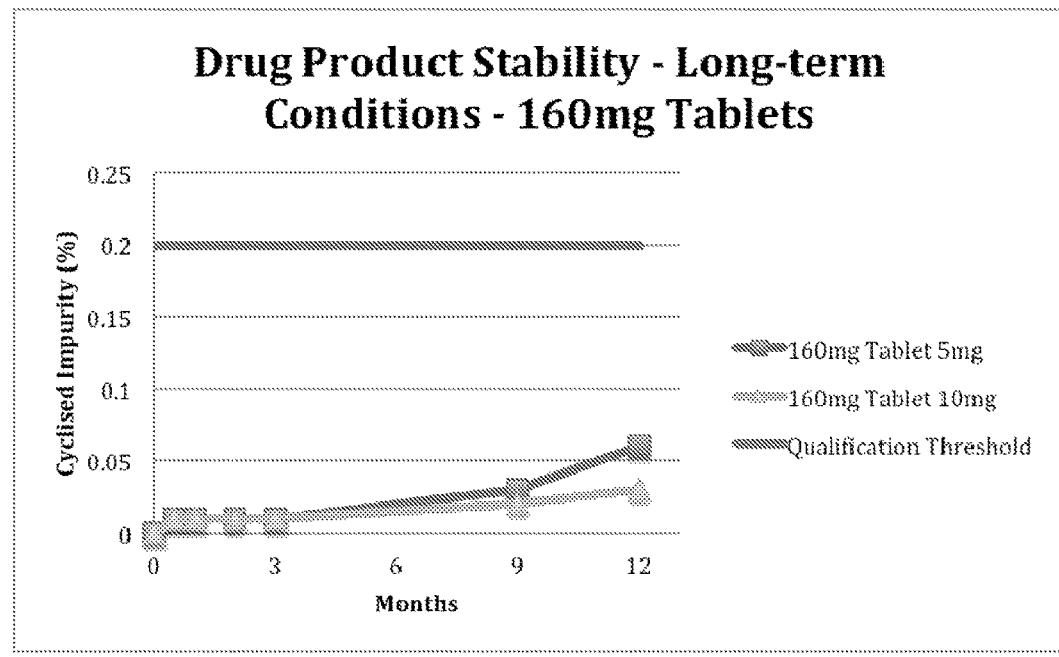
FIG. 2d shows drug stability data under long-term conditions for a 160 mg tablet formulation according to the invention against a qualification threshold of 0.2%.

The lactose capsule formulation showed a very small increase in the amount of cyclised impurity in the 2 mg strength in the first month, whereas the tablet formulation again demonstrated no increase in the amount of cyclised impurity. See FIGS. 2c and 2d.

Therefore, whilst the ORFADIN 5 mg and 10 mg capsules may achieve 12 months within specification at the long-term storage conditions, the accelerated conditions have demonstrated that they are highly sensitive to any increase in temperature due to increased cyclisation of the drug substance.

In contrast, the tablet formulation of the present invention has demonstrated stability at both the long-term and accelerated conditions, with no formation of the cyclised impurity observed. This shows that a room temperature storage condition is appropriate and the pharmaceutical product is not sensitive to an increase in the temperature due to the storage conditions.

Chromatographic Conditions

In the foregoing examples, the HPLC conditions were as follows:

TABLE 13

| HPLC conditions | |
|---|---|
| Mobile phase | 40 min gradient - see Table 14 |
| Mobile Phase A | 10 mM ammonium acetate, at pH 3.7 |
| Mobile Phase B | Acetonitrile |

TABLE 13-continued

HPLC conditions

| | |
|---|---|
| Column | Waters Sunfire C18 150 mm × 4.6 mm 3.5 μm |
| Injection volume | 20 μl |
| Flow rate | 1 ml/min |
| Detector | 257 nm |
| HPLC column | 25° C. |
| Run Time | 40 minutes |
| Retention Time | |
| Nitisinone | 27 minutes |
| 1,3-Cyclohexanedione | 2.7 minutes, RRT 0.10 |
| 2-nitro-4(trifluoromethyl) Benzioc acid | 7.0 minutes, RRT 0.26 |

TABLE 14

Gradient conditions of HPLC

| Time (minutes) | % A | % B |
|---|---|---|
| 0 | 20 | 80 |
| 30 | 57.5 | 42.5 |
| 30.1 | 90 | 10 |
| 35 | 90 | 10 |
| 35.1 | 20 | 80 |
| 40 | 20 | 80 |

The invention claimed is:

1. A pharmaceutical composition suitable for oral administration, consisting of nitisinone, lactose, and glyceryl dibehenate.

2. A pharmaceutical composition according to claim 1 in the form of a compressed tablet.

3. The pharmaceutical composition according to claim 1, wherein the composition is in the form of a compressed tablet.

4. The pharmaceutical composition according to claim 1, wherein the composition has an impurity stability of up to 0.5% impurity as measured by HPLC under ICH guidelines of at least 2 months at room temperature.

5. The pharmaceutical composition of claim 4, wherein the composition has an impurity stability of up to 0.2% impurity as measured by HPLC under ICH guidelines of at least 2 months at room temperature.

6. A method of treating tyrosinemia, comprising administering the pharmaceutical compositions of claim 1 to a patient in need thereof.

7. The method according to claim 6, wherein the tyrosinemia is Hereditary Tyrosinemia type-1 (HT-1), or alkaptonuria.

* * * * *